(12) United States Patent
Klima et al.

(10) Patent No.: US 6,290,692 B1
(45) Date of Patent: Sep. 18, 2001

(54) CATHETER SUPPORT STRUCTURE

(76) Inventors: Daniel J. Klima, 12055 41st. Ave., North, No. 223, Plymouth, MN (US) 55441; Paul J. Thompson, 9125 40 1/2 Ave., North, New Hope, MN (US) 55427

( * ) Notice: Subject to any disclaimer, the term of this patent is extended or adjusted under 35 U.S.C. 154(b) by 0 days.

(21) Appl. No.: 09/185,211

(22) Filed: Nov. 3, 1998

(51) Int. Cl.⁷ .............................. A61M 25/00; A61M 5/00
(52) U.S. Cl. .................... 604/524; 604/523; 604/525; 604/527; 604/264
(58) Field of Search ............................ 604/264, 523–28, 604/532–34; 606/194, 198; 138/125–25, 127, 143, 137–38, 140–41, 145–46

(56) References Cited

U.S. PATENT DOCUMENTS

| | | |
|---|---|---|
| 4,425,919 * | 1/1984 | Alston, Jr. et al. ................ 604/523 |
| 4,856,516 * | 8/1989 | Hillstead ................ 604/96 |
| 5,221,261 | 6/1993 | Termin et al. . |
| 5,222,949 * | 6/1993 | Kaldany ................ 604/523 |
| 5,476,508 | 12/1995 | Amstrup . |
| 5,507,767 * | 4/1996 | Maeda et al. ................ 606/198 |
| 5,628,787 | 5/1997 | Mayer . |
| 5,630,840 | 5/1997 | Mayer . |
| 5,645,559 | 7/1997 | Hachtman et al. . |
| 5,709,713 | 1/1998 | Evans et al. . |
| 5,713,947 | 2/1998 | Davidson . |
| 5,755,772 | 5/1998 | Evans et al. . |
| 5,766,238 * | 6/1998 | Lau et al. ................ 623/1 |
| 5,817,126 | 10/1998 | Imran . |
| 5,824,077 | 10/1998 | Mayer . |
| 5,827,242 * | 10/1998 | Follmer et al. ................ 604/523 |
| 5,836,962 | 11/1998 | Gianotti . |
| 5,857,069 | 1/1999 | Kohler . |
| 5,868,782 * | 2/1999 | Frantzen ................ 606/198 |
| 5,891,108 * | 4/1999 | Leone et al. ................ 604/264 |
| 5,951,495 * | 9/1999 | Berg et al. ................ 600/585 |
| 5,957,910 * | 9/1999 | Holden, II et al. ................ 604/527 |
| 5,968,070 * | 10/1999 | Bley et al. ................ 606/198 |
| 6,022,373 * | 2/2000 | Johnson et al. ................ 604/526 |
| 6,110,164 * | 8/2000 | Vidlund ................ 604/524 |

* cited by examiner

*Primary Examiner*—Angela D. Sykes
*Assistant Examiner*—Patricia M. Bianco

(57) ABSTRACT

The present disclosure relates to a catheter including a segment having a longitudinal axis, and a plurality of circumferential supports surrounding the axis. A plurality of filaments surround the circumferential supports to enhance torque transmission through the catheter segment.

15 Claims, 4 Drawing Sheets

CATHETER SUPPORT STRUCTURE

GOVERNMENT SUPPORT

This invention was made with Government support under Small Business Independent Research Grant HL60320, awarded by the National Institutes of Health. The Government has certain rights in the invention.

I. BACKGROUND OF THE INVENTION

1. Field of the Invention

This invention pertains to catheters for passage through a vasculature system. More particularly, this invention pertains to a novel construction of at least a segment of a catheter.

2. Description of the Prior Art

Catheters are widely used in medical treatment. A catheter is an elongated flexible member advanced through the vasculature system to a desired site. The catheter may be advanced over a previously inserted guide wire.

With the catheter in place, a wide variety of substances may be passed through the catheter to the site. For example, drugs may be moved through the catheter for site-specific drug delivery. Also, implements may be passed through the catheter. The catheter may also be used to remove fluids from the site. Still further, a catheter may be equipped with implements (e.g., balloon tips) for performing procedures (e.g., angioplasty) at the site.

Catheters have long been used in cardiovascular treatment. More recently, catheters are used in neurological procedures requiring advancement of the catheter through very narrow vessels. To accomplish these advances, a high degree of flexibility is desired. Also, catheters need very thin walls in order to retain an internal bore having as large a diameter as possible.

While advancing a catheter, a physician may twist a proximal end of the catheter in order to cause a corresponding twist of the distal end of the catheter (referred to as "torque transmission response"). A consistently reliable torque transmission response (e.g., a consistent one-to-one torque transmission response) is desired.

In designing catheters, it is desirable to provide a catheter which is kink resistant. Namely, a catheter typically is a tube with an internal bore of circular cross-section. When a catheter bends, it may be inclined to kink resulting in closure or geometric deformation of the circular bore. Such closure or deformation is undesirable. Further, in certain applications, the catheter may be subjected to high internal pressures (e.g., 300 psi). Such pressures tend to burst the catheter or expand the catheter geometry.

Catheter geometry can also by deformed by torque applied to the catheter. Many catheters are designed to have a reinforcing coil extending along the length of the catheter. If torque is applied in the direction of the coil winding, the internal diameter of the catheter may reduce. If torque is applied in the opposite direction, the diameter may expand. Dual coil catheters (i.e., catheters having two coils extending the length of the catheter with one coil being a clockwise wind and the other being a counter-clockwise wind) have been developed to retain dimensional stability regardless of direction of torque and to increase torque transmission. Unfortunately, such catheters are costly and have an extra layer of coil which takes up an already limited space within the vasculature. Thus a need exists to develop catheters that are kink resistant, able to transmit torque effectively and take up a minimal amount of space within the vasculature.

II. SUMMARY OF THE INVENTION

One aspect of the present invention relates to a catheter including a segment having a longitudinal axis, and a plurality of circumferential supports surrounding the axis. A plurality of filaments surround the circumferential supports. The circumferential supports assist in providing kink resistance, while the filaments provide enhanced torque and axial load transmission through the catheter segment.

III. BRIEF DESCRIPTION OF THE DRAWINGS

IV. DESCRIPTION OF THE PREFERRED EMBODIMENT

Referring now to the several drawing figures in which identical elements are numbered identically throughout, a description of a preferred embodiment of the present invention will now be provided.

Figure 1:
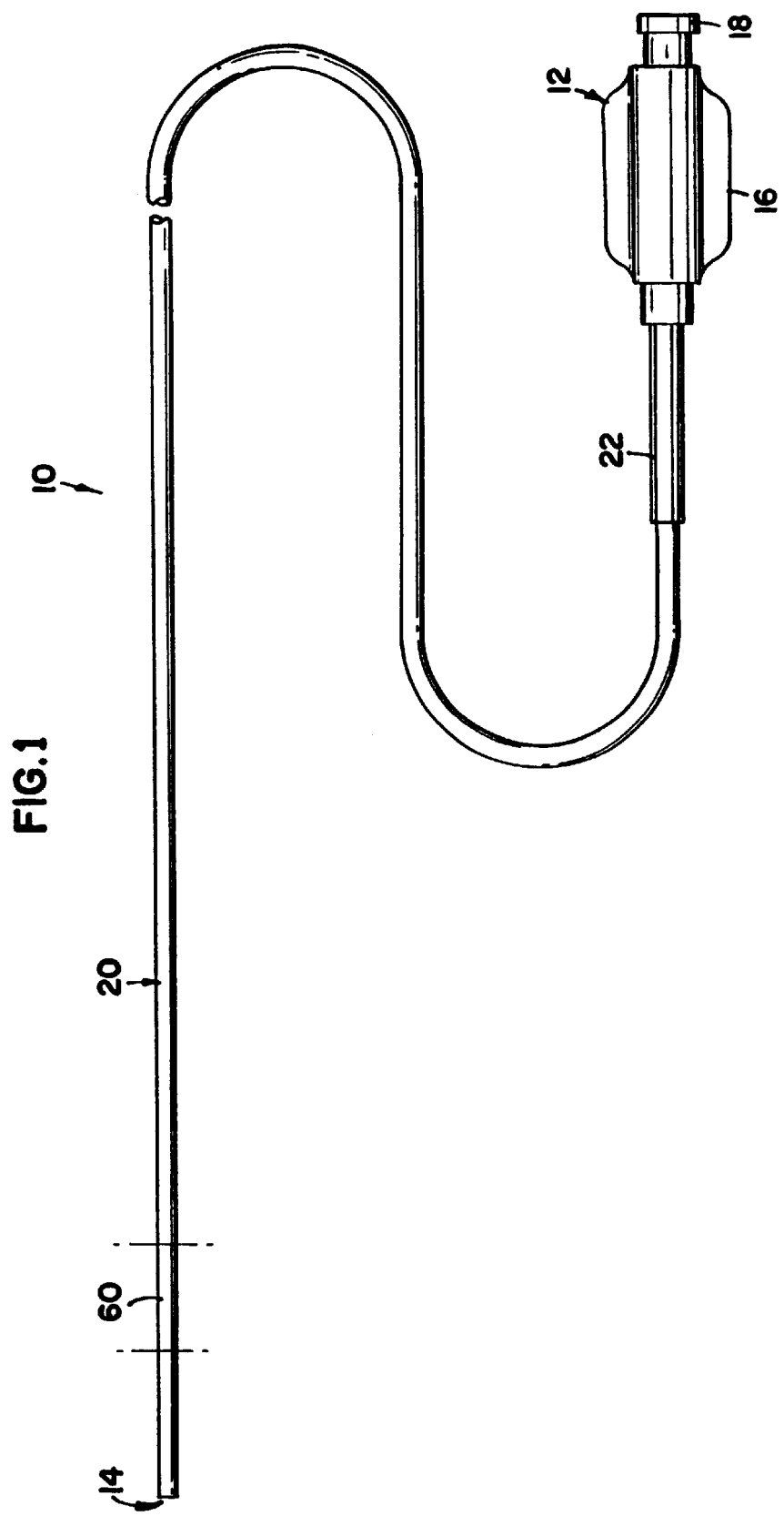
FIG. 1 is an overall view of a catheter according to the present invention.

FIG. 1 illustrates a catheter 10. The catheter 10 extends from a proximal end 12 to a distal end 14. At the proximal end 12, a hub 16 is provided to be gripped by a physician as well as having an inlet 18 for injection of fluids into the catheter 10. A flexible hollow shaft 20 is connected to the hub 16. The shaft 20 is sized to be inserted into a patient's vasculature. The shaft 20 is commonly about 150 cm long. A strain relief jacket 22 connects the shaft 20 to the hub 16. The foregoing description forms no part of this invention and is given to facilitate an understanding of the present invention.

The catheter 10 includes a segment 60 having the novel construction of the present invention. (For purposes of the remainder of this description, the word "catheter" is generally used to refer to the flexible shaft 20 of FIG. 1 having the segment 60 which a construction as will be described.) While the entire length of the catheter 10 can be constructed as will be described with reference to segment 60, it may be desirable to have a catheter 10 of multiple segments of different construction to impart different properties to different regions of the catheter 10 along its length. For example, it may be desirable to provide a catheter 10 having a proximal portion stiffer than a more flexible distal portion. While the present invention is suitable for forming catheter segments of varying degrees of flexibility and other properties, the present invention is described with reference to a segment 60 of the length of the catheter 10. This is to allow for catheters where the entire length is constructed according to the teachings of this application as well as catheters where only a discrete portion is so constructed and where the remainder is constructed according to conventional catheter construction techniques.

Figure 2:
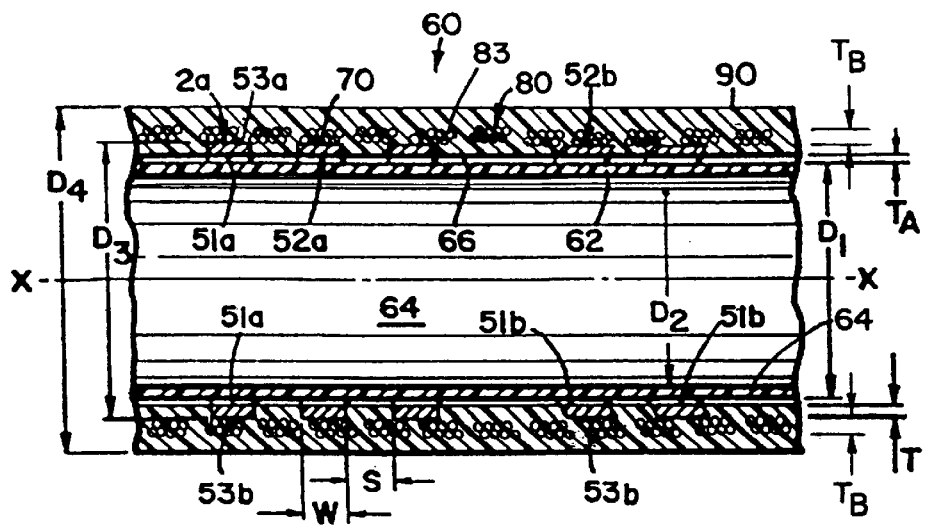
FIG. 2 is a cross-sectional, longitudinal view of a longitudinal segment of the catheter of FIG. 1.
Figure 3:
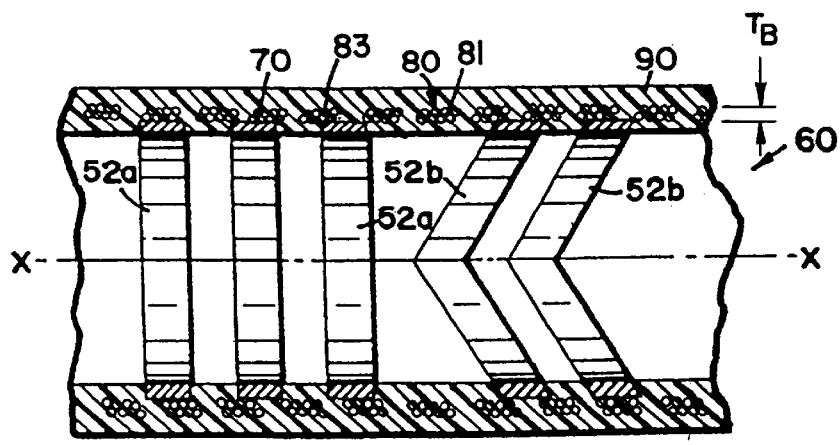
FIG. 3 is the view of FIG. 2 with the inner liner removed to expose circumferential supports of the catheter segment.

With reference to FIGS. 2 and 3, the segment 60 is shown to illustrate the novel construction. The segment 60 has a multi-layer construction including a flexible inner layer 62. By way of non-limiting example, the inner layer 62 is polytetraflouroethylene (PTFE) more commonly known by the trademark Teflon™. In a preferred embodiment, layer 62 has an outer diameter $D_1$ of 0.0230 inch (0.58 mm) and an inner diameter $D_2$ of 0.0210 inch (0.53 mm) to define an internal bore 64 surrounded by the Teflon inner tube layer 62.

The segment 60 also includes a circumferential support structure 70 as will be more fully described. The circumferential support structure 70 is generally tubular and is adhered to the external surface of the inner layer 62 by a thin bonding layer of any suitable adhesive 66 (e.g., polyurethane having a thickness $T_A$ of about 0.0004 inch or 0.01 mm). The circumferential support structure 70 has an outer diameter $D_3$ of about 0.025 inch (0.635 mm). The circumferential support structure 70 provides circumferential strength and kink resistance.

Surrounding the exterior of the circumferential support structure 70, a monofilament or a filament layer 80 is provided. The filament layer 80 is composed of a plurality of filaments 81 that are preferably arranged in one or more strands 83. The strands 83 are wrapped, intermeshed or braided about the support structure 70. The filaments 81 of each strand 83 can be twisted, plaited or laid parallel relative to one another. In one particular embodiment, the filaments 80 are laid parallel to one another to form a generally flat strip. Such a strip is advantageous because it can be wrapped flat about the circumference of the support structure 70 thereby minimizing the radial thickness occupied by the filaments.

The filaments 81 may be composed of any suitable flexible material which will provide torsional stiffness and axial strength to the segment 60. Such materials may include, for example, metal, plastics, polymers, nylon or other materials. A preferred material is a liquid crystal polymer sold under the name Vectran™ by Hoechst Celanese Corporation, of Charlotte, N.C. The filament layer 80 typically has a thickness $T_B$ of about 0.001–0.003 inch. The filament layer 80 provides enhanced torque transmission by increasing the torsional stiffness of the segment 60. The filaments 81 themselves are preferably limp or flexible. In certain embodiments, the filaments 81 can each have a diameter less than 0.001 inch, or about 0.0008 inch.

Surrounding the exterior of the filament layer 80, an outer polymer jacket 90 is provided. The outer jacket 90 may be any suitable flexible material for use in the vascular system. Such materials may be nylon or urethane. The outer jacket 90 has an outer diameter $D_4$ of 0.029 inch (0.74 mm).

In the foregoing, Applicants have provided a specific description of various layers of segment 60 as well as describing specific materials and dimensions. Such specificity has been given to describe a preferred embodiment of a specific catheter 10 utilizing the circumferential support structure 70 and filament layer 80 as will be described. More or fewer layers of materials could be used with the circumferential support structure 70 and filament layer 80 to impart desired properties (e.g., varying stiffness, strength, etc.) to segment 60. Similarly, specific materials and dimensions may be varied to alter the properties of segment 60. However, the combination of the circumferential support structure 70 and the filament layer 80 provides excellent kink resistance while still being capable of transmitting torque better than the circumferential support structure 70 alone.

Referring now to FIG. 3, the circumferential support structure 70 includes a plurality of circumferential supports 52a, 52b. Each of the supports 52a, 52b is a ring surrounding the axis X—X. The supports 52a, 52b may differ in shape for reasons that will be described. FIG. 3 illustrates that different shaped supports 52a, 52b may be included within segment 60 to alter properties (e.g., flexibility or torque transmission response along the length of segment 60). Alternatively, segment 60 could include circumferential supports which are of identical construction along its length (e.g., all having the shape of supports 52a) to impart more uniform properties to segment 60 along its length.

The circumferential supports 52a, 52b are positioned in parallel, spaced-apart alignment about axis X—X. Adjacent supports 52a, 52b are disjointed. Namely, each support 52a, 52b is an independent ring of rigid material. There is no rigid material (e.g., the material of rings 52a, 52b) interconnecting the rings 52a, 52b. Instead, adjacent rings are interconnected only by the flexible material of the liners 62, 90 and the filaments 80. Therefore, the rings 52a, 52b are non-integrally connected. As a result of the disjointed alignment of rings 52a, 52b, the segment 60 is highly flexible with the rings 52a, 52b providing structural integrity to retain the cross-sectional geometry of bore 64.

By way of example, the circumferential supports 52a, 52b have a width W of about 0.003 inch (0.076 mm). The width is the dimension parallel to the axis X—X. The circumferential supports 52a, 52b have a thickness T of about 0.001 inch (0.025 mm) (i.e., the radial dimension measured between the inner and outer surfaces 51a, 51b and 53a, 53b of the circumferential supports 52a, 52b). Finally, the circumferential supports 52a, 52b have an axial spacing S between opposing/adjacent supports 52a, 52b of about 0.005 inch (0.127 mm).

Figure 4:
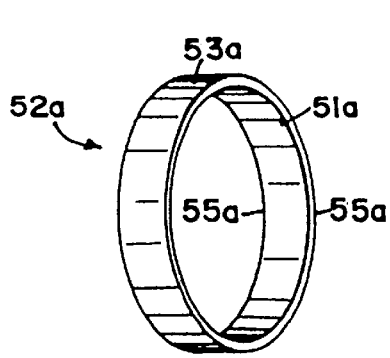
FIG. 4 is a perspective view of an embodiment of a circumferential support structure of the segment of FIG. 2.
Figure 5:
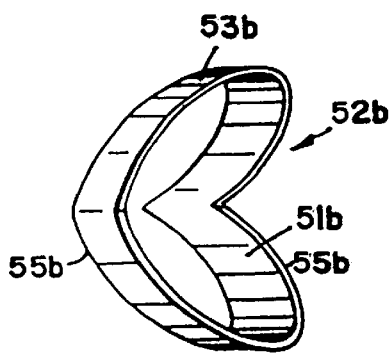
FIG. 5 is a perspective view of another embodiment of a circumferential support structure of the segment of FIG. 2.

FIGS. 4 and 5 illustrate two possible geometries of supports 52a, 52b. Since the supports 52a, 52b are formed by removing material from a cylindrical tube, the rings 52a, 52b are each complete circumferential surfaces surrounding the axis and are segments of a cylindrical tube. In FIG. 4, the ring 52a has parallel and planar axial ends 55a. In FIG. 5, the axial ends 55b are parallel but non-planar such that the ring 52b, in cross-section presents a V-shaped profile (see FIG. 3). Also, the circumferential supports 52a, 52b can be made narrower or thinner than the dimensions disclosed as well as changing the shape (as illustrated comparing FIGS. 4 and 5). Such modifications (as well as modifying the spacing S between supports 52a, 52b) alter the flexibility of segment 60. Therefore, the present invention provides a catheter designer with a wide variety of design options to use the present invention to fabricate catheters of varying properties for specific applications.

Figure 6:
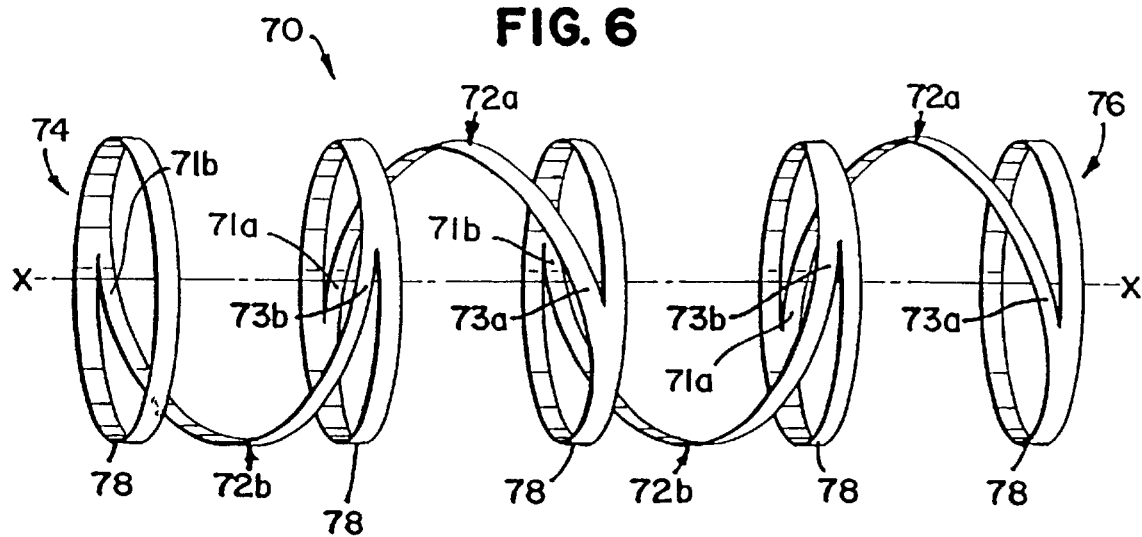
FIG. 6 is a perspective view of another embodiment of a circumferential support structure.

Referring to FIG. 6, an alternate circumferential support structure 70 includes a plurality of helical support struts 72a, 72b. As will become apparent, the plurality of support struts includes first and second sets of struts. Struts of the first set are designated 72a while struts of the second set are designated 72b.

While having an open structure, circumferential support structure 70 is generally tubular and extends from a first end 74 to a second end 76. The circumferential support structure 70 surrounds the longitudinal axis X—X. As indicated, the length of the circumferential support structure 70 (i.e., the distance between ends 74, 76) may be the entire length of the catheter or only a portion of the entire length.

Each of the struts 72a, 72b extends from a first end 71a, 71b to a second end 73a, 73b. The first and second ends 71a, 73a and 71b, 73b of a strut 72a, 72b are spaced apart longitudinally with respect to axis X—X. Additionally, each of the struts 72a, 72b curves around the axis X-X between ends 71a, 73a and 71b, 73b. In a typical embodiment shown in FIG. 6, the struts 72a, 72b are helical about axis X—X and curve substantially 360° about axis X—X.

Viewed from the first end 74 of the circumferential support structure 70, the struts 72a curve about axis X—X in a clockwise direction. Struts 72b curve in an opposite counter-clockwise direction.

In the embodiment shown, the struts 72a alternate in series with struts 72b along the length of the circumferential support structure 70. Adjacent ends 73a, 71b and 71a, 73b of adjacent struts 72a, 72b are connected such that all struts 72a, 72b along the length of circumferential support structure 70 are interconnected.

In the embodiment shown, a plurality of circumferential cylindrical rings or supports 78 are disposed between each of adjacent struts 72a, 72b. Accordingly, the adjacent ends 73a, 71b and 71a, 73b are not directly interconnected but, instead, are connected to opposite ends of a common circumferential support 78.

By way of example, the circumferential supports 78 and the struts 72a, 72b have a width of about 0.003 inch (0.076 mm). In the case of circumferential supports 78, the width is the dimension parallel to the axis X—X. In the case of the struts 72a, 72b, the width is the dimension transverse to the helical path of the struts 72a, 72b. The circumferential supports 78 and the struts 72a, 72b have a thickness T of about 0.001 inch (0.025 mm) (i.e., the radial dimension measured between the inner and outer diameters of the circumferential supports 78 and the struts 72a, 72b). Finally, the circumferential supports 78 have an axial spacing S between opposing/adjacent supports 78 of about 0.005 inch (0.127 mm).

Figure 7:
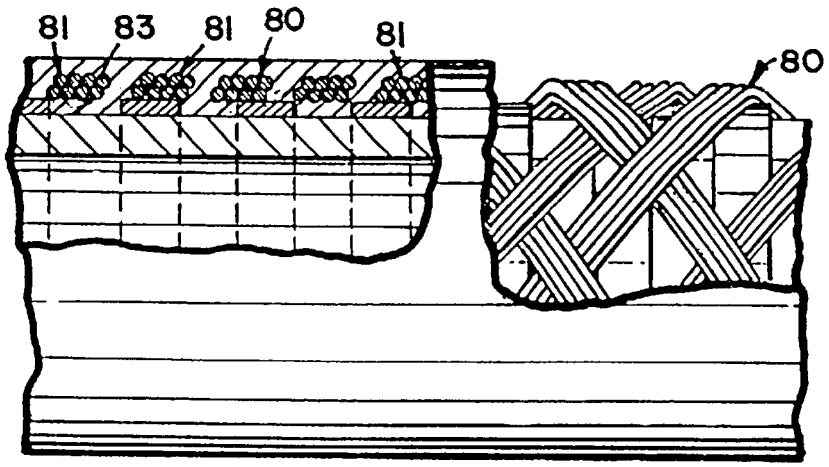
FIG. 7 is a cut-away view of the segment of FIG. 2.

Referring to FIGS. 2, 3, and 7, the filament layer 80 includes a plurality of filaments 81. The filaments 81 surround the circumferential support structure 70. The filaments 81 extend in both a circumferential direction and an axial direction relative to the longitudinal axis. Typically, the filaments 81 are interwoven and form a braid surrounding the circumferential support structure 70. The filament layer 80 functions to increase the torsional stiffness of the segment 60.

Preferably, the circumferential support structure 70 is fabricated from a solid blank of medical grade stainless steel tubing. Other possible materials include nickel-titanium alloys (e.g., nitinol) and cobalt-chromium-nickel alloys (e.g., Elgiloy™ alloy of Elgiloy, Inc. of Elgin, Ill., U.S.A.). Such a fabrication process includes starting with a rod (not shown) having an outer diameter equal to the desired inner diameter of the PTFE layer 62. The PTFE layer 62 is placed over the rod which acts as a jig to hold the elements of catheter 10 during fabrication. The adhesive 66 is applied to the external surface of PTFE layer 62. A solid tube of medical grade stainless steel (referred to as a hypotube) is then adhered to PTFE layer 62 by adhesive 66. As an alternative, the PTFE layer 62 and the metal tube can be assembled without the adhesive 66 with parts held in alignment until the final outer layer 90 is applied.

The solid metal tube is then milled to remove excess material of the tube as waste and leaving only the material of the circumferential supports 78, and struts 72a, 72b or the circumferential supports 52a and 52b as the circumferential support structure 70. In a typical embodiment, the metal tube is milled by a chemical milling process. In such a process, a pattern mask of the desired pattern of the circumferential supports 78 and struts 72a, 72b or the circumferential supports 52a, 52b is placed over the metal tube. A light source sensitizes a photoresist applied to the metal to create a pattern on the metal tube matching the mask. The photosensitized tube is then chemically etched to dissolve away the areas of the tube corresponding to the waste leaving only the desired material of the circumferential supports 78 and struts 72a, 72b or the circumferential supports 52a, 52b. It will be appreciated that this description of a chemical milling of the metal tube forms no part of this invention per se. Such a process is more fully described in commonly assigned and copending U.S. patent application Ser. No. 08/645,607 the specification of which was published on Dec. 5, 1996 as International Publication No. WO96/38193 or PCT International application Ser. No. PCT/US96/08232.

After the tube is so milled, the filament 80 layer is applied to or wrapped about the outer surface of the circumferential support structure 70. The outer layer 90 is then applied over the filament 80 layer. The material of the outer layer 90 may, at the option of a designer, fill in the axial spacing S between the circumferential supports 52, 78 and filaments 81 or leave such spacing as voids to enhance flexibility. The rod is then removed from the PTFE layer 62 leaving a completed segment 60.

The present invention has been described in a preferred embodiment and may be modified while keeping with the teachings of the present invention. For example, the circumferential support structure 70 need not be formed of metal or fabricated in the chemical milling manner indicated. The circumferential support structure 70 can be formed from any structural material in any manner including, without limitation, electrical discharge machining, laser cutting, or assembly of individual components.

Similarly, while a preferred circumferential support structure 70 has been disclosed, numerous modifications can be made to the structure to vary the properties of the catheter 10 to meet design objectives for a specific application. For example, geometry of the support rings can be varied (e.g., thicker, wider, narrower, closer or more distant spacing as well as non-symmetrical shapes compared to the symmetrical shapes shown) to vary strength and flexibility.

Figure 8:
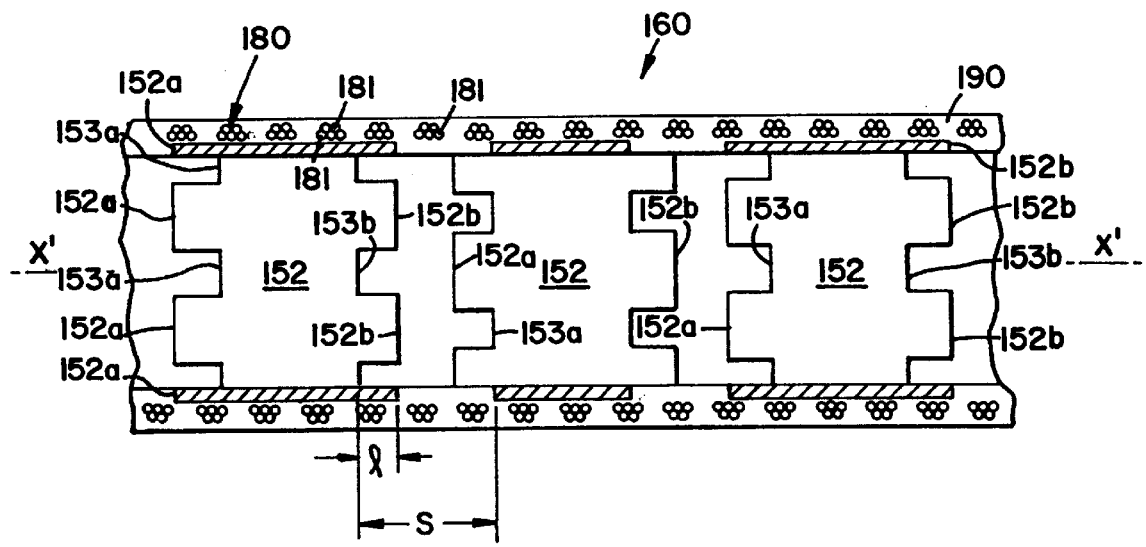
FIG. 8 is a cross-sectional, longitudinal view of a longitudinal segment of an alternative catheter with the inner liner removed to expose circumferential supports of the catheter segment.

FIG. 8 shows a longitudinal cross-sectional view of a catheter segment 160 that is a further embodiment of the present invention. The catheter segment 160 includes a plurality of circumferential supports 152 mounted on flexible inner liner (not shown) and surrounded by a flexible outer jacket 190.

Figure 9:
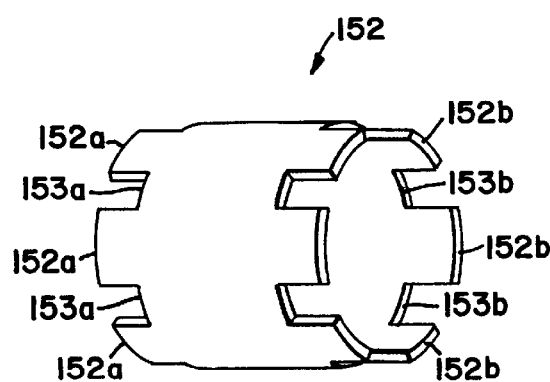
FIG. 9 is a perspective view of one of the circumferential supports of the catheter segment of FIG. 8.

FIG. 9 shows a single one of the circumferential supports 152 in isolation from the liners. As shown in FIG. 8, the circumferential supports 152 are positioned in parallel, spaced apart alignment along a longitudinal axis X'—X' and each comprises an independent ring.

Distal and proximal projections 152a and 152b project axially or longitudinally outward from opposite axial ends of each circumferential support 152. Adjacent circumferential supports 152 are disjointed. The axial projections 152a and 152b extend in a direction generally parallel to the longitudinal axis X'—X'. Gaps 153a are formed between the distal projections 152a, while gaps 153b are formed between the proximal projections 152b.

Adjacent circumferential supports 152 are positioned in different circumferential or rotational orientations about the longitudinal axis X'—X'. For example, as shown in FIG. 8, the projections 152a and 152b of adjacent circumferential supports 152 are not in axial alignment with one another. Instead, the axial projections 152a are aligned with the axial gaps 153b, and the axial projections 152b are aligned with the axial gaps 153a. The axial projections 152a and 152b are preferably larger than the gaps 153a and 153b to inhibit meshing between the circumferential supports 152. However, in alternative embodiments, adjacent rings can be configured to intermesh with one another. For example, axial projections of one ring can fit between the axial projections of an adjacent ring. In still other embodiments, rings can be used that have only proximal axial projections, or only distal axial projections.

As shown in FIG. 8, the catheter segment 160 also includes a filament layer 180 including a plurality of filaments 181 similar to those previously described in the specification. The filaments 181 surround the circumferential supports 152 and extend in both a circumferential direction and an axial direction relative to the longitudinal axis X'—X'. In certain embodiments, the filaments 181 can be interwoven to form a braid surrounding the circumferential supports 152. In other embodiments, the filaments 181 can be aligned parallel to one another to form a strip-like structure.

In the embodiment of FIGS. 8 and 9, the axial projections 152a and 152b preferably have lengths l in a range of 0.005–0.010 inches, and an unloaded spacing S (i.e., a spacing when no torque or axial load is being applied to the catheter segment) of 0.010–0.025 inches preferably exists between the circumferential supports 152. The segment 160 can be manufactured by a similar process to that described above with respect to the embodiment of FIGS. 2–5 and 7.

From the foregoing, the present invention has been disclosed in a preferred embodiment. The invention permits construction of a catheter overcoming disadvantages of prior designs as well as providing a structure having various features which can be modified to design catheters with optimum performance for a wide variety of applications. It is intended that modifications and equivalents of the disclosed concepts, such as those which readily occur to one of skill in the art shall be included within the scope of the claims appended hereto.

What is claimed is:

1. A catheter including a segment having a longitudinal axis, said segment comprising:
    a plurality of circumferential supports surrounding said axis;
    each of said plurality of circumferential supports being axially spaced from all others of said plurality of circumferential supports; and
    each of said plurality of circumferential supports being a continuous ring having a complete circumferential surface surrounding said axis; and
    a plurality of filaments surrounding said circumferential supports.

2. A catheter according to claim 1, said segment further comprising an elongated inner liner positioned within the circumferential supports.

3. A catheter according to claim 2, said segment further comprising a flexible outer layer surrounding an outer surface of said circumferential supports.

4. A catheter according to claim 2, wherein the filaments have components extending in both a circumferential direction and an axial direction relative to the longitudinal axis.

5. A catheter according to claim 1, wherein said segment is sized to fit within a blood vessel.

6. A catheter according to claim 1, wherein said segment further includes an inner layer of flexible material surrounded by said circumferential supports and an outer layer of flexible material surrounding said circumferential supports, said inner layer having an inner surface defining at least a portion of a catheter bore.

7. A catheter according to claim 1, wherein said circumferential supports are cylindrical rings.

8. A catheter according to claim 1, wherein the filaments are interwoven and form a braid surrounding the circumferential supports.

9. A catheter according to claim 1, wherein said circumferential supports comprise rings connected by segments of helical coils.

10. A catheter according to claim 1, wherein the filaments provide means for increasing a torsional stiffness of the segment.

11. A catheter according to claim 1, wherein the filaments are interwoven.

12. A catheter according to claim 1, wherein each of said circumferential supports has a first end and a second end, at least one of said first end and said second end having axial projections and axial gaps.

13. A catheter including a segment having a longitudinal axis, said segment comprising:
    a tubular inner liner surrounding said axis;
    a plurality of circumferential supports surrounding said inner liner;
        each of said plurality of circumferential supports being axially spaced from all others of said plurality of circumferential supports; and
        each of said plurality of circumferential supports being a continuous ring having a complete circumferential surface surrounding said axis;
    a plurality of interwoven filaments forming a braid that surrounds the circumferential supports; and
    an outer polymeric jacket that covers the circumferential supports and the braid.

14. A catheter including a segment having a longitudinal axis, said segment comprising:
    a tubular inner liner surrounding said axis;
    a plurality of circumferential supports surrounding said inner liner;

each of said plurality of circumferential supports being axially spaced from all others of said plurality of circumferential supports; and each of said plurality of circumferential supports being a continuous ring having a complete circumferential surface surrounding said axis;

a strand comprising a plurality of filaments; said strand surrounding said circumferential supports in a helical fashion to form a plurality of wraps, each of said plurality of wraps being axially spaced from an adjacent one of said plurality of wraps; and an outer polymeric jacket that covers the circumferential supports and the braid.

15. A catheter including a segment having a longitudinal axis, said segment comprising:

a plurality of circumferential supports surrounding said axis:

each of said plurality of circumferential supports being axially spaced from all others of said plurality of circumferential supports; and each of said plurality of circumferential supports being a continuous ring having a complete circumferential surface surrounding said axis;

said plurality of circumferential supports embedded in a polymeric jacket; and a plurality of filaments surrounding said circumferential supports, said plurality of filaments embedded in said polymeric jacket.

* * * * *